(12) United States Patent
Swanson

(10) Patent No.: US 8,831,746 B2
(45) Date of Patent: *Sep. 9, 2014

(54) SELF-FOLDING PADDLE LEAD AND METHOD OF FABRICATING A PADDLE LEAD

(75) Inventor: John W. Swanson, Portland, OR (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 329 days.

This patent is subject to a terminal disclaimer.

(21) Appl. No.: 13/169,879

(22) Filed: Jun. 27, 2011

(65) Prior Publication Data

US 2011/0257714 A1   Oct. 20, 2011

Related U.S. Application Data

(60) Continuation of application No. 12/573,425, filed on Oct. 5, 2009, now Pat. No. 7,970,480, which is a division of application No. 11/673,001, filed on Feb. 9, 2007, now abandoned.

(60) Provisional application No. 60/772,321, filed on Feb. 10, 2006.

(51) Int. Cl.
*A61N 1/00* (2006.01)
*A61N 1/05* (2006.01)

(52) U.S. Cl.
CPC .................................. *A61N 1/0553* (2013.01)
USPC .......................................................... 607/117

(58) Field of Classification Search
CPC ..... A61N 1/05; A61N 1/0422; A61N 1/0553; A61N 1/0551; A61N 1/058; A61N 1/36071

USPC .................... 607/50, 115, 145, 149, 150, 117
See application file for complete search history.

(56) References Cited

U.S. PATENT DOCUMENTS

| 5,000,194 A | 3/1991 | van den Honert et al. |
| 5,158,537 A | 10/1992 | Haak et al. |
| 5,800,500 A | 9/1998 | Spelman et al. |
| 6,024,702 A | 2/2000 | Iversen |

(Continued)

FOREIGN PATENT DOCUMENTS

| EP | 1818074 | 2/2002 |
| WO | 2005092432 | 10/2005 |

OTHER PUBLICATIONS

European Patent Office, International Search Report for PCT/US2007/067642 dated Dec. 10, 2007.

*Primary Examiner* — Christopher D Koharski
*Assistant Examiner* — Roland Dinga

(57) ABSTRACT

In one embodiment, a medical lead comprises a lead body for conducting electrical pulses and a paddle. The paddle includes an intermediate metal layer, at least an insulative polymer backing layer, and an insulative polymer covering layer. The intermediate metal layer comprises a plurality of features defined by gaps in the metal material in the metal layer such that each feature is electrically isolated from each other feature, wherein each feature includes a respective connector element that is electrically coupled to at least one conductor within the lead body, wherein a portion of the insulative polymer covering layer is exposed above each feature to define a respective electrode for the corresponding feature. Also, the paddle possesses shape memory to cause the paddle to assume a substantially planar orientation when the shape memory is in a relaxed state.

7 Claims, 8 Drawing Sheets

(56) References Cited

U.S. PATENT DOCUMENTS

| | | |
|---|---|---|
| 6,374,143 B1 | 4/2002 | Berrang et al. |
| 6,415,187 B1 | 7/2002 | Kuzma et al. |
| 6,522,932 B1 * | 2/2003 | Kuzma et al. ............... 607/116 |
| 6,624,510 B1 | 9/2003 | Chan et al. |
| 6,678,564 B2 | 1/2004 | Kettrl et al. |
| 6,719,582 B1 | 4/2004 | Swanson |
| 6,757,970 B1 | 7/2004 | Kuzma et al. |
| 6,782,619 B2 | 8/2004 | Corbett et al. |
| 6,895,283 B2 | 5/2005 | Erickson et al. |
| 6,919,633 B2 | 7/2005 | Perlov et al. |
| 6,976,998 B2 | 12/2005 | Rizzo et al. |
| 7,085,605 B2 | 8/2006 | Bluger et al. |
| 7,107,097 B2 | 9/2006 | Stern et al. |
| 7,107,104 B2 | 9/2006 | Keravel et al. |
| 7,177,702 B2 | 2/2007 | Wallace et al. |
| 7,620,246 B2 | 11/2009 | Akahori |
| 7,697,995 B2 | 4/2010 | Cross et al. |
| 2002/0022873 A1 | 2/2002 | Erickson et al. |
| 2002/0111661 A1 | 8/2002 | Cross et al. |
| 2003/0040785 A1 | 2/2003 | Maschino et al. |
| 2003/0158588 A1 | 8/2003 | Rizzo et al. |
| 2003/0204228 A1 * | 10/2003 | Cross et al. ............... 607/116 |
| 2004/0022440 A1 | 2/2004 | Akahori |
| 2004/0243205 A1 | 12/2004 | Keravel et al. |
| 2005/0070972 A1 | 3/2005 | Wahlstrand et al. |
| 2005/0154435 A1 | 7/2005 | Stern et al. |
| 2005/0203602 A1 | 9/2005 | Wallace et al. |
| 2005/0288758 A1 | 12/2005 | Jones et al. |
| 2007/0027514 A1 | 2/2007 | Gerber |

* cited by examiner

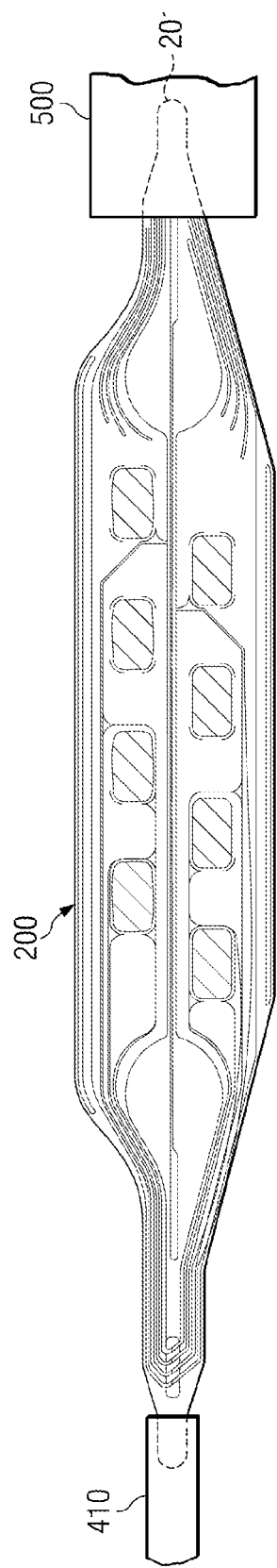
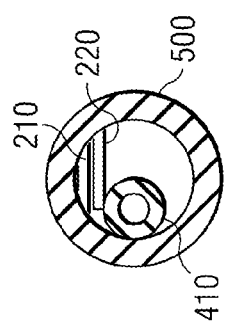
FIG. 5F
FIG. 5G

SELF-FOLDING PADDLE LEAD AND METHOD OF FABRICATING A PADDLE LEAD

RELATED APPLICATION

This application is a continuation of U.S. application Ser. No. 12/573,425 filed Oct. 5, 2009, now U.S. Pat. No. 7,970,480, which is a divisional of U.S. application Ser. No. 11/673,001 filed Feb. 9, 2007, abandoned, which claims the benefit of U.S. Provisional Application No. 60/772,321, filed Feb. 10, 2006, which is incorporated herein by reference.

TECHNICAL FIELD

The present application is generally related to a paddle lead that is self-folding for insertion in a patient using an insertion tool or catheter and that returns to an extended state upon exiting the insertion tool or catheter within the epidural space.

BACKGROUND

Application of electrical fields to spinal nerve roots, spinal cord, and other nerve bundles for the purpose of chronic pain control has been actively practiced for some time. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

It is known that each exterior region, or each dermatome, of the human body is associated with a particular longitudinal spinal position. Thus, electrical stimulation of nerve tissue must occur at a specific longitudinal location to effectively treat chronic pain. Additionally, it is important to avoid applying electrical stimulation of nerve tissue associated with regions of the body that are unaffected by chronic pain. Positioning of an applied electrical field relative to a physiological midline is also important.

Percutaneous leads and laminotomy leads are the two most common types of lead designs that provide conductors that deliver stimulation pulses from an implantable pulse generator (IPG) to distal electrodes adjacent to the nerve tissue. As shown in FIG. 1A, conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, conventional laminotomy or paddle lead 150 has a paddle configuration and typically possesses a plurality of electrodes 151 (commonly, two, four, eight, or sixteen) arranged in one or more columns. Multi-column laminotomy leads enable reliable positioning of a plurality of electrodes. Also, laminotomy leads offer a more stable platform that tends to migrate less after implantation and that is capable of being sutured in place. Laminotomy leads also create a uni-directional electrical field and, hence, can be used in a more electrically efficient manner than conventional percutaneous leads. Due to their dimensions and physical characteristics, conventional laminotomy leads require a surgical procedure for implantation. The surgical procedure (a partial laminectomy) is evasive and requires the resection and removal of certain vertebral tissue to allow both access to the dura and proper positioning of a laminotomy lead.

SUMMARY

In one embodiment, a medical lead comprises a lead body for conducting electrical pulses and a paddle. The paddle includes an intermediate metal layer, at least an insulative polymer backing layer, and an insulative polymer covering layer. The intermediate metal layer comprises a plurality of features defined by gaps in the metal material in the metal layer such that each feature is electrically isolated from each other feature, wherein each feature includes a respective connector element that is electrically coupled to at least one conductor within the lead body, wherein a portion of the insulative polymer covering layer is exposed above each feature to define a respective electrode for the corresponding feature. Also, the paddle possesses shape memory to cause the paddle to assume a substantially planar orientation when the shape memory is in a relaxed state.

The foregoing has outlined rather broadly certain features and/or technical advantages in order that the detailed description that follows may be better understood. Additional features and/or advantages will be described hereinafter. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 5A-5H depict placement of a paddle lead within the epidural space of a patient according to one representative embodiment.

DETAILED DESCRIPTION

Figure 2:
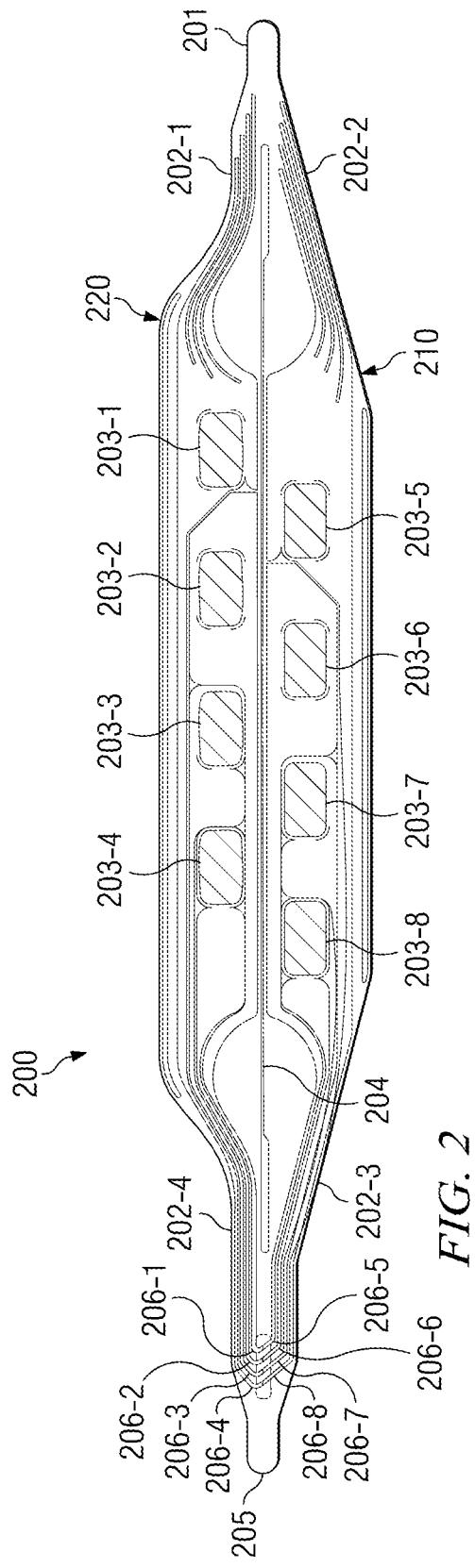
FIG. 2 depicts a self-folding flexible paddle according to one representative embodiment.

FIG. 2 depicts a schematic representation of flexible paddle 200 according to one representative embodiment. Flexible paddle 200 is preferably fabricated using laminated layers of biocompatible polymer(s) and one or several thin layers of suitable conductive material. The conductive material may cover almost all of the surface area of the polymer backing. Specifically, the various structures (electrodes, guides, connector elements) are preferably defined by scribing or etching borders or edges between these structures. In such embodiments, the conductive material provides sufficient shape memory to cause the paddle structure to assume a planar shape in a relaxed state. In alternative embodiments, one or more layers of the polymer may be utilized to provide the desired mechanical characteristic.

The width of paddle 200 is sufficient to provide suitable spacing between the two sets of electrodes 203 to enable stimulation of the pertinent nerve fibers across the physiological midline of the patient. The design of paddle 200 enables paddle 200 to be substantially maintained at a desired position within the patient's epidural space. Moreover, the design of paddle 200 ensures that electrodes 203-1 through 203-8 will remain in fixed relative positions, e.g., electrodes 203-1 through 203-4 cannot be offset longitudinally from electrodes 203-5 through 203-8.

Paddle 200 includes guide structures 202-1 and 202-2 which are proximate to distal end 201 of the paddle. Guide structures 202-1 and 202-2 cause paddle 200 to fold upon itself when the guide structures 200 contact the lumen of an insertion tool. In some embodiments, the guide structures 202-1 and 202-2 are implemented by scribing longitudinal elements in the conductive material. When paddle 200 contacts the inner surface of the insertion tool, the longitudinal elements distribute force into the body of paddle 200 according to the shape of the respective longitudinal elements. Additionally, guide structures 202-1 and 202-2 are preferably implemented to possess different amounts of rigidity (e.g., due to the shape of the respective guide structures 202, the thickness of their respective longitudinal members, etc.). The difference in the amount of rigidity controls the manner in which paddle 200 folds. As will be discussed in greater detail below, one side of paddle 200 folds over the other side in a substantially lateral manner thereby minimizing the amount of open space within the epidural space required for paddle 200 to unfold.

In the embodiment shown in FIG. 2, paddle 200 includes slit 204 in the middle of the lead paddle to provide a portion of the paddle with a very small modulus. Slit 204 may be defined by removing at least the conductive material. If the outer insulative material provides an undue amount of rigidity at this point, the insulative material may also be removed or replaced with a lower modulus material with improved elasticity. When distal end 201 is initially inserted within a suitable insertion tool, guide structures 202-1 and 202-2 experience force associated with the contact with the inner wall of the insertion tool. The force associated the contact and the presence of slit 204 cause segment 210 of paddle 200 to fold over segment 220. In one embodiment, after paddle 200 has been folded, the entire width of paddle 200 is fit within the insertion tool. Thus, the paddle can be advanced through the tool into the patient's epidural space. Also, once the paddle is pushed through the insertion tool, the shape memory characteristics of the laminate structure cause paddle 200 to unfold thereby exposing electrodes 203-1 through 203-8 to the spinal tissue. Preferably, the shape memory provides sufficient force to displace fibrous tissue or scar tissue within the epidural space. However, the expansive force of the shape memory is also preferably limited to avoid damage to other tissue. In some embodiments, one or more laminate film layers and/or the conductive material cause paddle 200 to possess memory or a spring characteristic.

In a similar manner, if paddle 200 needs to be removed from the patient, distal end 205 and guide structures 202-2 and 202-3 are provided. Specifically, proximal end 205 can be pulled by lead body 410 into the same or similar tool as used to insert paddle lead 200. When guide structures 202-2 and 202-3 experience force due to contact of paddle 200 with the inner wall of the tool, segment 210 once again folds over segment 220 thereby enabling paddle 200 to be withdrawn from the patient's epidural space through the tool. Accordingly, it is not necessary to perform a partial laminectomy procedure for the insertion or removal of paddle 200.

Numerous variations upon the design shown in FIG. 2 are possible. For example, paddle 200 need not include slit 204. The center portion of paddle 200 could be rigid and both of segments 210 and 220 could fold when paddle 200 is inserted into an insertion tool. Alternatively, slit 204 could be moved from the middle of the paddle. Also, multiple slits 204 could be used to create multiple folding segments. Also, slit 204 need not necessarily remain as a void between the front and back sides of paddle 200. Instead, the conductive material and/or the original insulative material may be removed and a relatively thin portion of highly elastic polymer or hydrogel material, as examples, may be provided at slit 204 to prevent tissue growth from occurring through paddle 200.

Also, paddle 200 could include more than two segments with all or some of the segments folding when inserted into a suitable tool. Although eight electrodes are shown in FIG. 2, any suitable number of electrodes could be employed. Additionally, any suitable pattern of electrodes could be formed. In some embodiments, multiple (three, four, five, etc.) columns of electrodes are employed to enable "field steering" which is known in the art to facilitate selective stimulation of nerve tissues. Also, although folding is the preferred mechanism to reduce the width of paddle 200 during insertion procedures, other deformations could be alternatively employed. For example, paddle 200 could be adapted to "curl" into a cylindrical structure upon entry into the insertion tool and "uncurl" upon exiting the tool.

Figure 1A:
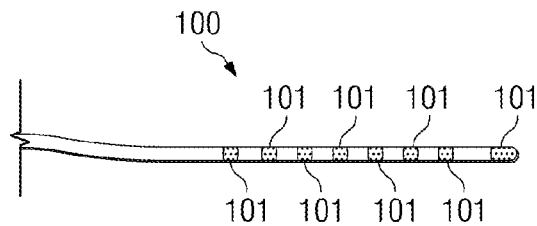
FIGS. 1A and 1B depict a conventional percutaneous lead and a conventional paddle lead, respectively.
Figure 1B:
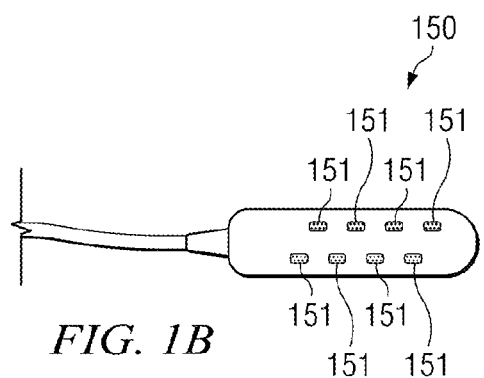
Figure 3:
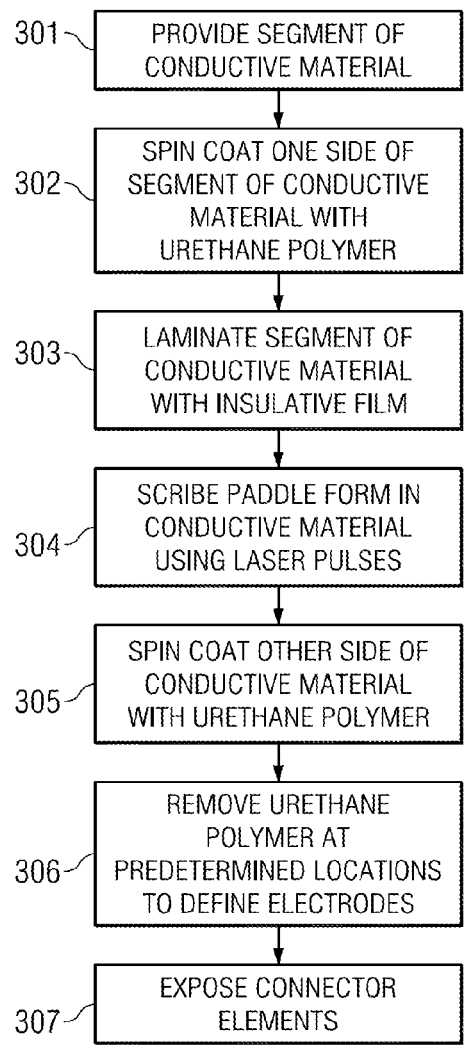
FIG. 3 depicts a flowchart for fabricating the paddle shown in FIG. 2 according to one representative embodiment.

FIG. 3 depicts a flowchart for fabricating paddle 200 according to one representative embodiment. In step 301, a rectangle or other suitable portion of conductive material is provided. Although the following discussion only refers to fabrication of a single paddle 200, multiple paddles can be fabricated in parallel on suitably sized portion of conductive material according to the present invention. The conductive material can be medical grade stainless steel, platinum iridium, and/or the like. The thickness of the conductive material is selected to allow the conductive material to be relatively flexible while possessing a degree of memory or spring characteristic. In one embodiment, the thickness of the conductive material is selected to equal approximately 25.4 microns (1 mil).

In step 302, a coating of urethane (or a similar polymer) is spin coated on one side of the conductive material for the purpose of achieving a surface with greater adhesive qualities. In step 303, a urethane film (or any other suitable biocompatible polymer) is applied to the same side as the spin coat and is laminated to the conductive material. The urethane film and coating provide an insulative layer to electrically isolate the conductive material. The urethane film preferably has a thickness of preferably 25.4 to 152.4 microns (one to six mils).

In step 304, the paddle form is created by scribing the paddle form in the conductive material using a suitable laser (e.g., a programmable YAG laser system). A separate strip or "feature" of conductive material is defined in a pattern definition for each electrode that extends from a respective connector element 206 (shown collectively as 206-1 through 206-8 in FIG. 2) to the area where the corresponding electrode will be formed (as will be discussed below). In addition to defining the conductive paths, the laser scribing defines the guide structures that facilitate the self-folding functionality of paddle 200. It shall be appreciated that the guide structures (as well as any structure providing spring-like properties) need not be conductive.

The pattern definition is preferably provided to a programmable laser system. The programmable laser system then applies pulses of energy according to the defined pattern to ablate the conductive material between each strip of conductive material. The application of laser pulses is controlled to ablate the conductive material at the defined locations without cutting completely through the urethane film behind the ablated conductive material. The lamination between the urethane film and the conductive material holds the separate strips or features of conductive material at the defined locations. Also, upon completion of the application of laser pulses to paddle 200, each strip of conductive material is electrically isolated from every other strip or feature due to the laser scribed separations between them and the insulative characteristic of the urethane film. In an alternative embodiment, photo-etching techniques could be employed to create the paddle form. For example, the paddle form could be created using a photoresist and chemical etching in lieu of laser scribing. In another alternative embodiment, micro-printing is employed to create the paddle form.

In step 305, a spin coat of urethane is applied over the conductive material on the side opposite to the urethane laminate layer. The coating of the urethane material electrically insulates the top of paddle 200. In step 306, electrodes 203 are defined by removing the urethane material of the applied coating at the respective locations thereby exposing the conductive material at those locations. The removal of the urethane material may occur using the programmable laser. Alternatively, a separate $CO_2$ laser could be utilized for exposure of the conductive material and/or masked plasma etching. In step 307, connector elements 206 are exposed on one or both sides of paddle 200.

After the completion of paddle 200 according to the flowchart of FIG. 3, paddle 200 is ready to be mechanically integrated with and electrically coupled to a medical lead. To provide electrical connections between an implantable pulse generator and electrodes 203 of paddle 200, the medical lead provides a plurality of conductors (e.g., wires) which are typically spirally wound around a mandrel. Each conductor is contained within an insulative material to ensure that the plurality of conductors are electrically isolated from each other. Also, the plurality of conductors are typically enclosed within a protective flexible body of biocompatible and biostable polymer. On a proximal end of the medical lead, a plurality of terminals are provided for coupling a pulse generator device to the various conductors.

On the distal end of a medical lead, openings in the outer body and in the insulative coating of the conductors are made at suitable locations. Conductive material can be provided within the openings to provide an electrical path from the conductors to the surface of the lead. The exposed connector elements 206 of paddle 200 are preferably coupled to the lead conductors at these locations to create the electrical connection between the conductors of the lead and electrodes 203. Alternatively, a wire connection could be employed between each conductor of the lead and a respective connector element 206. Additional details regarding specific medical leads and lead fabrication methods are available in U.S. Pat. No. 6,216, 045 entitled "Implantable lead and method of manufacture," which is incorporated herein by reference. It shall be appreciated that paddle designs according to the present invention can be implemented with any type of suitable medical lead.

Figure 4A:
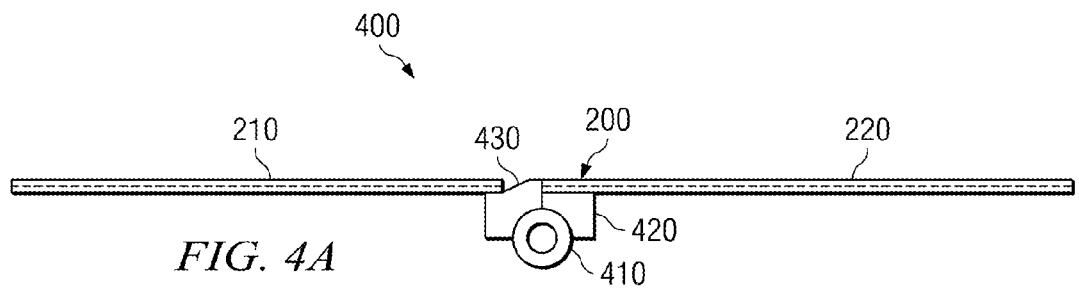
FIG. 4A depicts a cross-sectional view of a paddle lead including the paddle shown in FIG. 2 according to one representative embodiment.

FIG. 4A depicts a cross-sectional view of paddle lead assembly 400 according to one representative embodiment. Medical lead 410 is shown at the bottom of the assembly. Block 420 is utilized to facilitate the lead assembly process and as shown in FIG. 4A, is affixed to medical lead 410. Block 420 can be implemented using an extrusion of bio-compatible polymer. Block 420 could also be implemented as an injection molded structure. Paddle 200 is coupled to block 420. Block 420 may optionally include recess 430 that facilitates the folding of segment 210. It shall be appreciated that other shapes and designs could be employed for block 420. Also, in an alternative embodiment, paddle 200 could be directly attached to a stimulation lead.

Figure 4B:
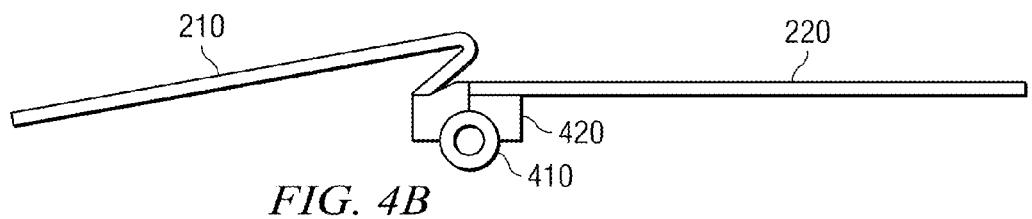
FIGS. 4B-4D depict the "sliding" folding progression of the paddle of the paddle lead shown in FIG. 4A according to one representative embodiment.
Figure 4C:
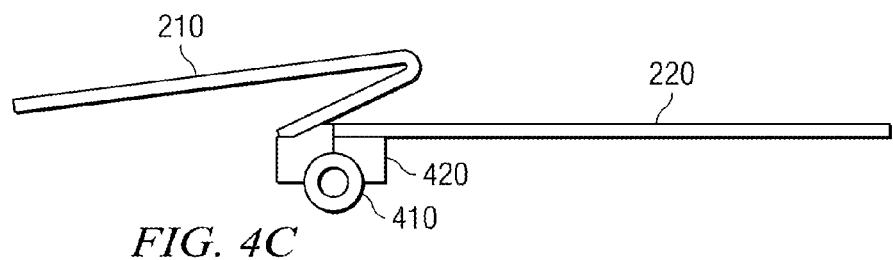
Figure 4D:
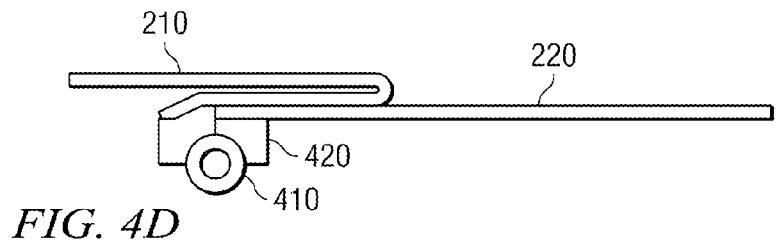
Figure 7:
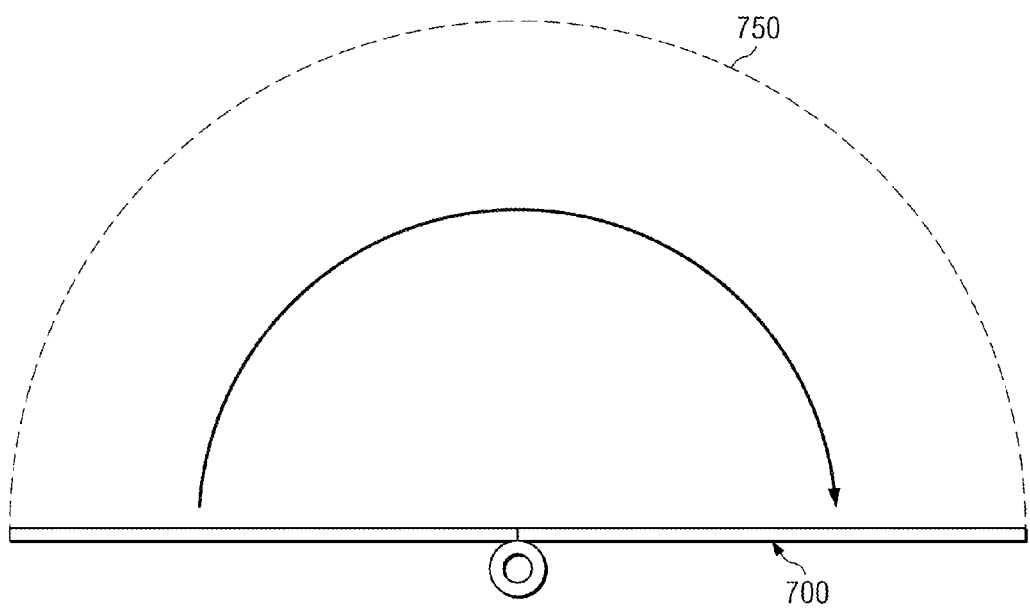
FIG. 7 depicts a foldable paddle lead that folds in a manner similar to a page being turned in a book.

One advantage of assembly 400 is the minimization of volume displacement associated with the folding and unfolding of the paddle. Reference is made to FIG. 7 for comparison, where foldable lead 700 folds in a manner similar to turning pages in a book. As shown in FIG. 7, this type of folding requires free space 750 to accomplish the folding and unfolding. Specifically, if foldable lead 700 were inserted into the epidural space of a patient, space 750 must be free of tissue to allow foldable lead 700 to unfold. However, assembly 400 is adapted to fold in a different manner that requires significantly less volume displacement. Recess 430 and the slit 204 enables portion 210 of paddle 200 to fold over portion 220 in a "sliding" or substantially lateral manner. Slit 204 provides a degree of flexibility to the paddle and recess 430 guides portion 210 during the folding process. As shown in the progression of FIGS. 4B through 4D, the upward displacement of portion 210 of paddle 200 during folding (and, similarly, during unfolding) is relatively minimal. That is, a "bend" develops in portion 210 which is moved across the portion of the paddle 200 during the folding and unfolding process. Accordingly, assembly 400 can be unfolded within a much smaller volume than foldable lead 700.

Figure 5A:
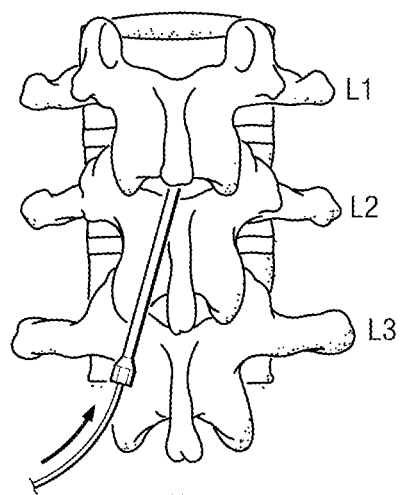
Figure 5B:
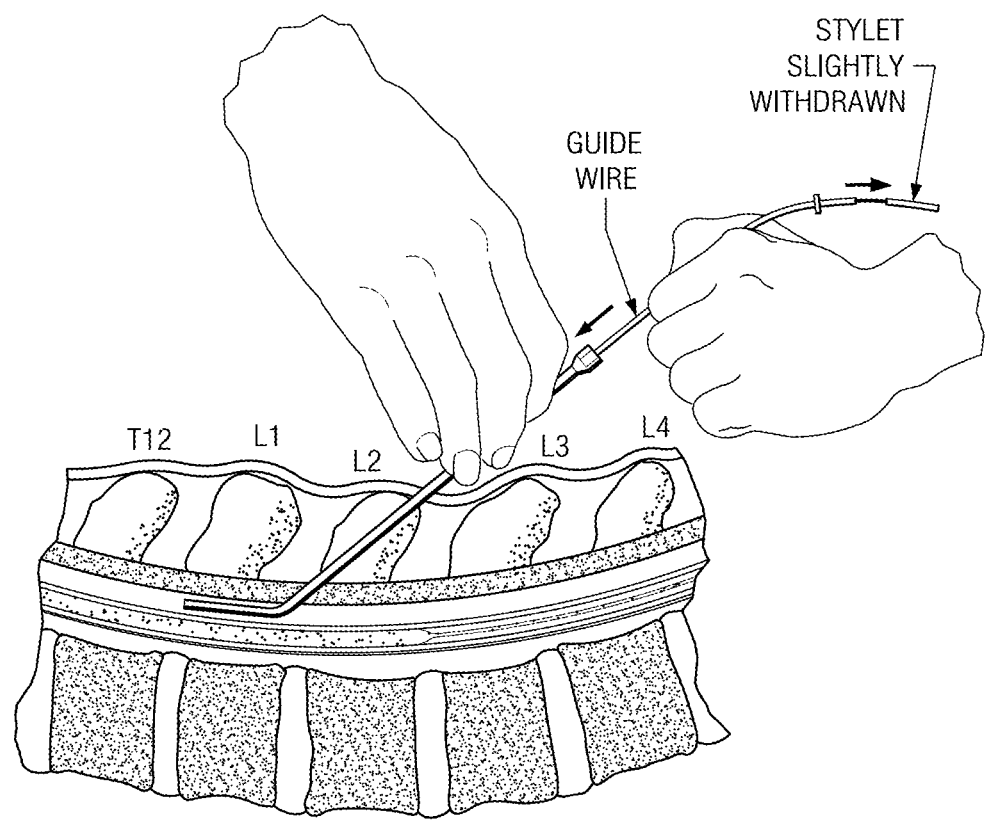
Figure 5C:
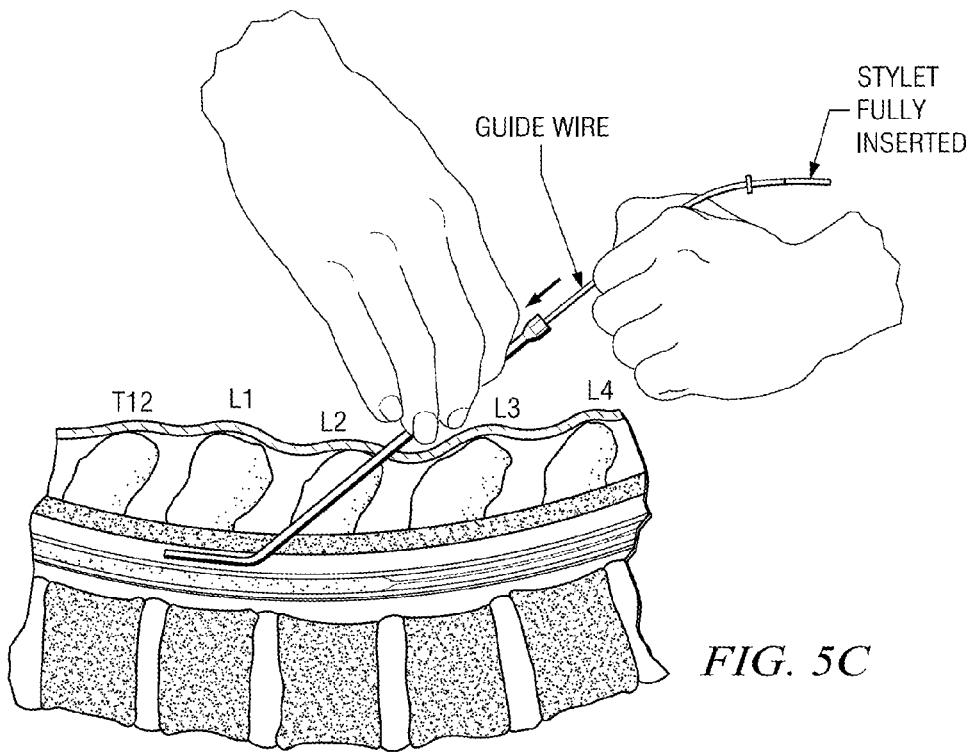

FIGS. 5A-5H depict various steps of a method for placement of a paddle lead within the epidural space of a patient according to one representative embodiment. As shown in FIG. 5A, an epidural needle is inserted into the epidural space. The initial insertion of the epidural needle typically occurs an angle that is offset relative to the spinal column. Also, the location for insertion of the needle is typically two to five vertebrae below the spinal tissue associated with the pain to be treated by the electrical neuromodulation. Using fluoroscopic guidance, a guide wire is inserted with the stylet slightly withdrawn as shown in FIG. 5B. Once the tip of the guide wire is fully within the epidural space and slightly beyond the distal tip of the needle, the stylet is fully reinserted and the guide wire is advanced to the desired target location as shown in FIG. 5C.

Figure 5D:
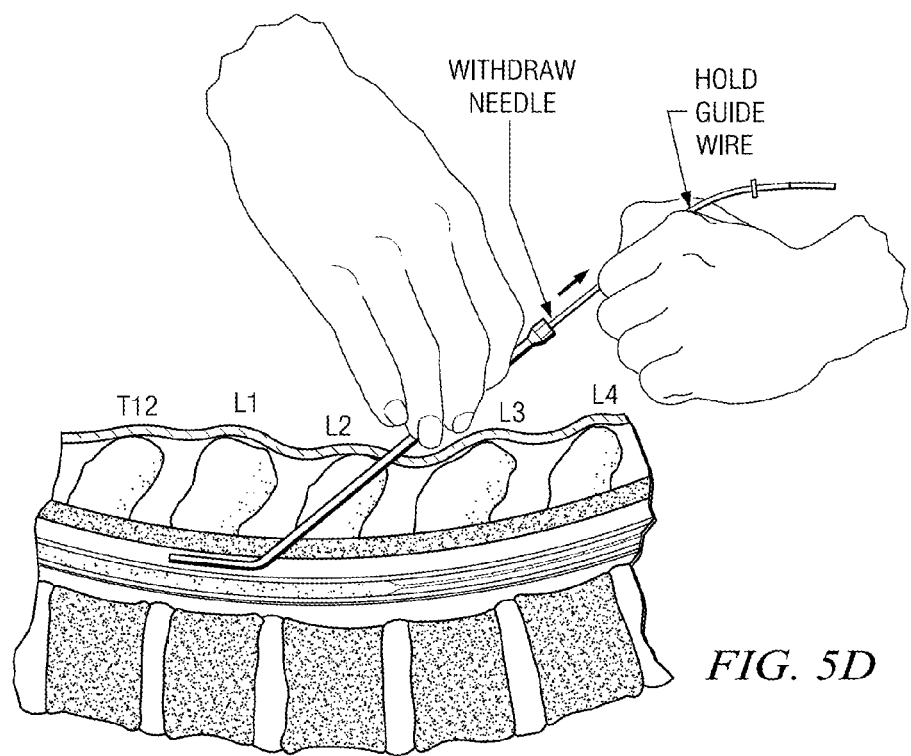
Figure 5E:
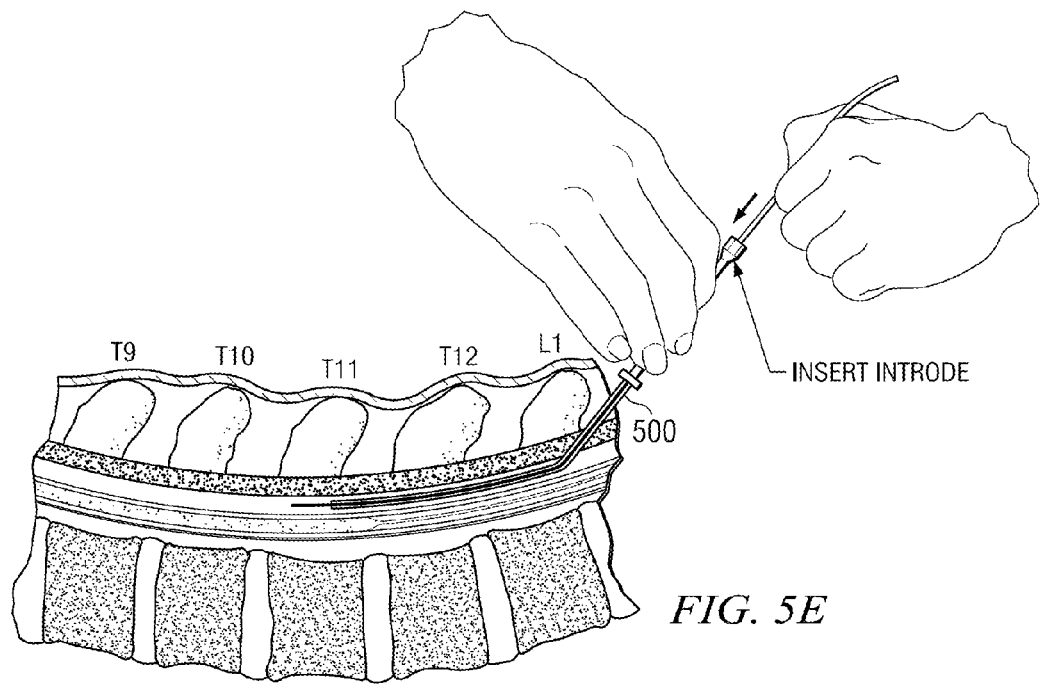

As shown in FIG. 5D, the needle is removed using the "hold-and-push" technique leaving the guide wire in the epidural space. The insertion tool 500 is inserted over the proximal end of the guide wire and advanced into the epidural space under fluoroscopy to appropriate position (FIG. 5E) and the guide wire is removed. For the purpose of the present application, an insertion tool refers to any catheter-like structure, having a lumen or an open channel, that can be inserted between the vertebrae into the epidural space without a partial laminectomy. The insertion tool may or may not comprise a sharp distal end. The insertion tool preferably expands the tissue surrounding the guide wire thereby enabling the insertion of the paddle lead. In practice, the insertion tool is preferably a flexible hollow plastic tube. The flexibility of the tube accommodates an offset insertion angle into the vertebrae used for the initial insertion of the epidural needle. An example of an introduction tool can be found in U.S. Patent Publication No. 20050288758A1, which is incorporated herein by reference. If appropriate, a segment of the epidural space could be opened to accommodate paddle 200 (step not shown). For example, a cutting tool (e.g., having dual blades or scissor-like elements) could be advanced through insertion tool 500 to open tissue to allow paddle 200 to be received and unfolded.

Figure 5H:
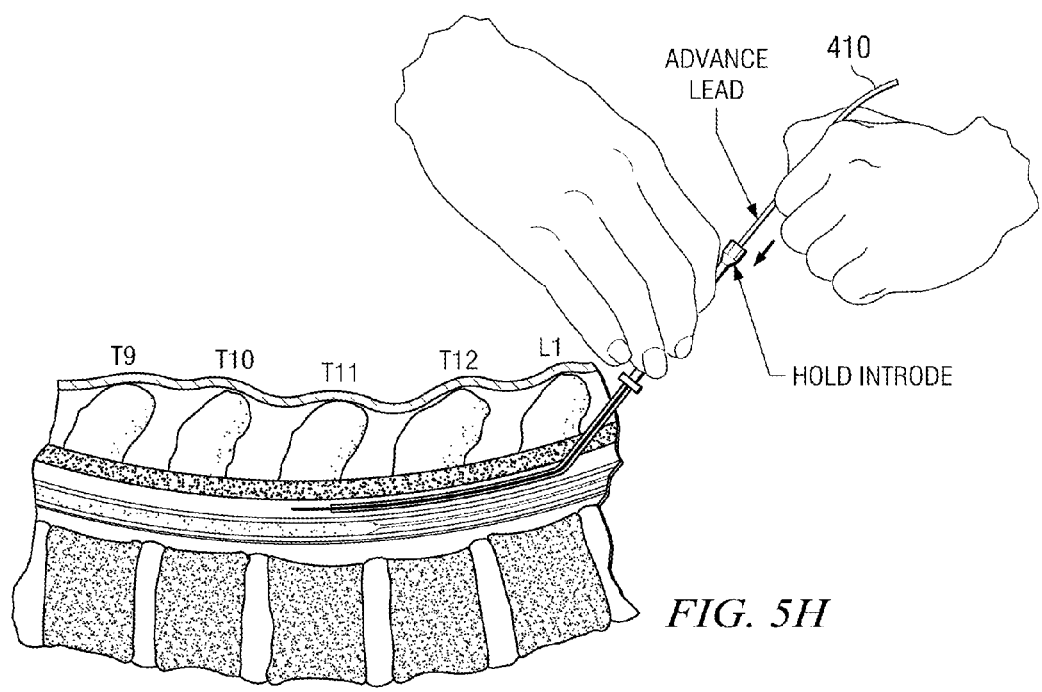

The distal end of paddle 200 of lead assembly 400 is inserted within insertion tool 500 as shown in FIG. 5F. Preferably, a guide wire is inserted within the lumen of the lead coupled to paddle 200 to facilitate the advancement of the lead and paddle. The contact of paddle 200 with the interior of insertion tool 500 causes paddle 200 to fold upon itself thereby fitting paddle 200 within the insertion tool as shown in FIG. 5G. Paddle 200 is advanced through insertion tool 500 by advancing lead body 410 as shown in FIG. 5H. When paddle 200 exits insertion tool 500, paddle 200 resumes its extended state to expose electrodes 203 to the target spinal tissue for stimulation. In an alternative embodiment, the lead could be mated to the insertion tool using a suitable mating component and the lead could be advanced concurrently with the placement of the insertion tool.

Figure 6:
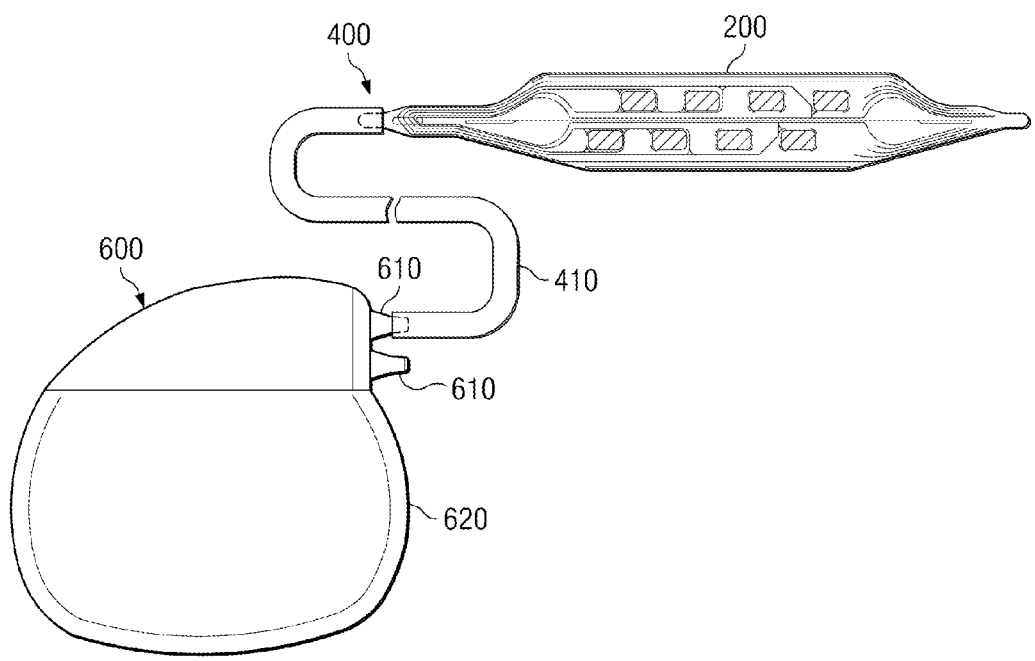
FIG. 6 depicts a foldable paddle lead coupled to an implantable pulse generator according to one representative embodiment.

FIG. 6 depicts foldable paddle lead 400 coupled to implantable pulse generator (IPG) 600 according to one representative embodiment. An example of a commercially available IPG is the Eon® Rechargeable IPG available from Advanced Neuromodulation Systems, Inc. As shown in FIG. 6, paddle lead 400 is coupled to one of the headers 610 of generator 600. Each header 610 electrically couples to a respective lead 410 or an extension lead. Also, each header 610 electrically couples to internal components contained within the sealed portion 620 of IPG 600. The sealed portion 620 contains the pulse generating circuitry, communication circuitry, control circuitry, and battery (not shown) within an enclosure to protect the components after implantation within a patient. The control circuitry controls the pulse generating circuitry to apply varying pulses to the patient via electrodes 203 of paddle 200 according to multiple parameters (e.g., amplitude, pulse width, frequency, etc.). The parameters are set by an external programming device (not shown) via wireless communication with IPG 600.

Although some representative embodiments have been discussed in terms of neurostimulation applications, alternative representative embodiments could be employed for other medical applications. For example, in one alternative embodiment, a paddle structure could be adapted for any suitable type of cardiac stimulation such as defibrillation and pacing. The paddle structure could be inserted through the vascular system of the patient using a suitable catheter and introduced within a suitable cardiac region. The paddle structure then could be adapted to unfold upon exiting the catheter to contact the cardiac tissue to be stimulated. In other alternative embodiments, the paddle could be utilized for cardiac mapping and/or tissue ablation.

Some representative embodiments may provide a number of advantages. Some representative embodiments provide a paddle that can be inserted into and removed from the epidural space of a patient without requiring a partial laminectomy. Furthermore, some representative embodiments provide a method of fabricating a paddle design that is highly repeatable and efficient. The fabrication method further does not necessarily require the use of any overly caustic chemicals.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

The invention claimed is:

1. A method for fabricating a stimulation lead for electrical stimulation of tissue of a patient, comprising:
providing a prefabricated lead body for conducting electrical pulses through a plurality of conductors;
providing a thin-film paddle for delivering the electrical pulses from the plurality of conductors to tissue of the patient, wherein (i) the paddle comprises a metal layer laminated to at least one insulative layer, the at least one insulative layer being a thin film of flexible, foldable polymer material, (ii) the metal layer comprises a plurality of electrically isolated features defined by gaps in the metal layer, (iii) each feature formed by a continuous planar strip of conductive material extending from a proximal end of the paddle with a portion of the respective continuous planar strip exposed through insulative material of the paddle forming an electrode of the paddle; (iv) the electrodes of the features are organized in a first longitudinal portion and a second longitudinal portion of the metal layer;
providing a support structure; and
mechanically coupling the paddle and the lead body to the support structure, wherein the thin-film paddle comprises a proximal portion for terminating each of the plurality of features with a respective connector element for electrical and mechanical connection to one of the plurality of conductors of the prefabricated lead body.

2. The method of claim 1 wherein the paddle comprises guide structures that provide a differential amount of rigidity to the first and second longitudinal portions such that contact of a distal end of the paddle with a lumen of an insertion tool causes the first portion to fold over the second portion and causes the first portion to unfold, upon exit from the lumen, in a substantially lateral manner relative to a plane in which the paddle is disposed.

3. The medical lead of claim 2 wherein a first set of the guide structures are disposed on a first side of the paddle structure and a second set of the guide structures are disposed on a second side of the paddle structure.

4. The medical lead of claim 2 wherein the first set of guide structures comprises an amount of curvature that differs from an amount of curvature of the second set of guide structures.

5. The medical lead of claim 1 wherein the metal layer comprises a longitudinal slit.

6. The medical lead of claim 1 wherein the longitudinal slit is covered by an elastic material having a reduced modulus relative to insulative material covering a remaining portion of the paddle.

7. The medical lead of claim 6 wherein the elastic material covering the slit is a hydrogel material.

* * * * *